United States Patent
Quallich et al.

[11] Patent Number: 5,968,950
[45] Date of Patent: Oct. 19, 1999

[54] APO B-SECRETION/MTP INHIBITOR HYDROCHLORIDE SALT

[75] Inventors: George J. Quallich, North Stonington; George Chang, Ivoryton; Lewin T. Wint, Old Saybrook, all of Conn.

[73] Assignee: Pfizer Inc, New York, N.Y.

[21] Appl. No.: 09/033,506

[22] Filed: Mar. 2, 1998

Related U.S. Application Data

[60] Provisional application No. 60/050,514, Jun. 23, 1997.

[51] Int. Cl.⁶ .................................................... A01N 43/42
[52] U.S. Cl. ........................ 514/310; 514/307; 546/143; 546/144
[58] Field of Search .................................. 514/310, 307; 546/144, 143

[56] References Cited

U.S. PATENT DOCUMENTS

4,022,900  5/1977  Mathison .............................. 424/258

FOREIGN PATENT DOCUMENTS

| | | |
|---|---|---|
| 0106140 | 8/1988 | European Pat. Off. . |
| 0584446 | 3/1994 | European Pat. Off. . |
| 0643057 | 3/1995 | European Pat. Off. . |
| WO 9626205 | 8/1996 | WIPO . |
| WO 96/40640 | 12/1996 | WIPO . |
| WO 9823593 | 6/1998 | WIPO . |

OTHER PUBLICATIONS

Wetterau, John R. et al., "Localization of intracellular triacylglycerol and cholesteryl ester transfer activity in rat tissues" *Biochimica et Biophysica Acta*, 875, 1986, pp. 610–617.

Wetterau, John R. et al, "Absence of Microsomal Triglyceride Transfer Protein in Individuals with Abetalipoproteinemia" *Science*, vol. 258, Nov. 6, 1992, pp. 999–1001.

*Primary Examiner*—Dwayne C. Jones
*Attorney, Agent, or Firm*—Peter C. Richardson; Gregg C. Benson; A. Dean Olson

[57] ABSTRACT

A hydrochloride salt of an Apo B secretion/MTP inhibitor, methods of making the salt, methods of using the salt and pharmaceutical compositions containing the salt are disclosed.

16 Claims, 3 Drawing Sheets

APO B-SECRETION/MTP INHIBITOR HYDROCHLORIDE SALT

This application claims priority to provisional application U.S. Ser. No. 60/050,514 filed Jun. 23, 1997, the benefit of which is hereby claimed under 37 C.F.R. §1.78(a)(3).

BACKGROUND OF THE INVENTION

This invention relates to compounds which are inhibitors of microsomal triglyceride transfer protein (MTP) and/or apolipoprotein B (Apo B) secretion and which are, accordingly, useful for the prevention and treatment of atherosclerosis and its clinical sequelae, for lowering serum lipids, and in the prevention and treatment of related diseases. More particularly, this invention relates to an Apo B secretion/MTP inhibitor hydrochloride salt, pharmaceutical compositions comprising this salt, a process for preparing this salt and to methods of treating atherosclerosis, obesity, and related diseases and/or conditions with the salt.

Microsomal triglyceride transfer protein catalyzes the transport of triglyceride, cholesteryl ester, and phospholipids and has been implicated as a putative mediator in the assembly of Apo B-containing lipoproteins, biomolecules which contribute to the formation of atherosclerotic lesions. Specifically, the subcellular (lumen of the microsomal fraction) and tissue distribution (liver and intestine) of MTP have led to speculation that it plays a role in the assembly of plasma lipoproteins, as these are the sites of plasma lipoprotein assembly. The ability of MTP to catalyze the transport of triglyceride between membranes is consistent with this speculation, and suggests that MTP may catalyze the transport of triglyceride from its site of synthesis in the endoplasmic reticulum membrane to nascent lipoprotein particles within the lumen of the endoplasmic reticulum.

Compounds which inhibit MTP and/or otherwise inhibit Apo B secretion are accordingly useful in the treatment of atherosclerosis and other conditions related thereto. Such compounds are also useful in the treatment of other diseases or conditions in which, by inhibiting MTP and/or Apo B secretion, serum cholesterol and triglyceride levels may be reduced. Such conditions may include, for example, hypercholesterolemia, hypertriglyceridemia, pancreatitis, and obesity; and hypercholesterolemia, hypertriglyceridemia, and hyperlipidemia associated with pancreatitis, obesity, and diabetes. For a detailed discussion, see for example, Wetterau et al., Science, 258, 999–1001, (1992), Wetterau et al., Biochem. Biophys. Acta., 875, 610–617 (1986), European patent application publication No. 0 584 446 A2, and European patent application publication No. 0 643 057 A1 the latter of which discloses certain compounds of the generic formulae

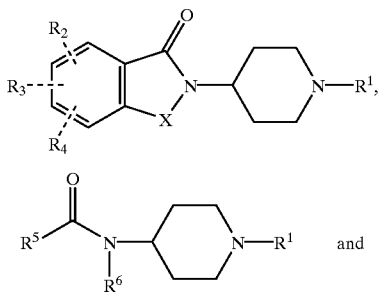

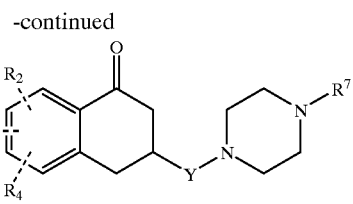

which have utility as inhibitors of MTP.

Also, commonly assigned PCT publication WO 96/40640 (published Dec. 19, 1996) discloses certain MTP inhibitors having the generic structure

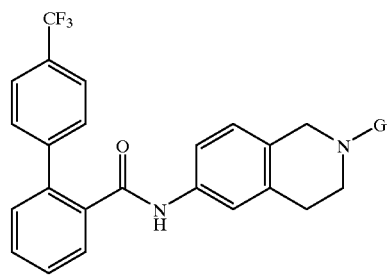

Thus, although there are a variety of atherosclerosis therapies, there is a continuing need and a continuing search in this field of art for alternative therapies.

SUMMARY OF THE INVENTION

This invention is directed to the salt of Formula I

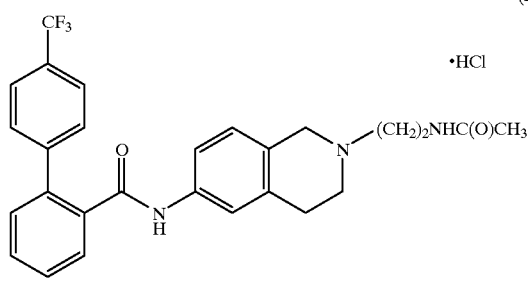

Alternatively, the above salt is named as 4'-trifluoromethylbiphenyl-2-carboxylic acid-[2-(2-acetylaminoethyl)-1,2,3,4-tetrahydroisoquinolin-6-yl]-amide hydrochloride.

Another aspect of this invention is directed to the corresponding anhydrous HCl salt.

Another aspect of this invention is directed to the corresponding monohydrate HCl salt.

Another aspect of this invention is directed to a corresponding anhydrous HCl salt polymorph having the X-ray powder diffraction pattern as shown in FIG. 1.

A preferred dosage is about 0.001 to 100 mg/kg/day of the Formula I compound. An especially preferred dosage is about 0.01 to 10 mg/kg/day of the Formula I compound.

This invention is also directed to pharmaceutical compositions which comprise a therapeutically effective amount of a salt of Formula I and a pharmaceutically acceptable carrier.

This invention is also directed to pharmaceutical compositions for the treatment of atherosclerosis, pancreatitis, obesity, hypercholesterolemia, hypertriglyceridemia, hyperlipidemia or diabetes, which comprise a therapeutically effective amount of a salt of Formula I or a hydrate thereof and a pharmaceutically acceptable carrier or diluent.

This invention is also directed to pharmaceutical compositions for the treatment of atherosclerosis in a mammal (including a human being) which comprise an atherosclerosis treating amount of a salt of Formula I or a hydrate thereof and a pharmaceutically acceptable carrier.

This invention is also directed to pharmaceutical compositions for the treatment of pancreatitis in a mammal (including a human being) which comprise a pancreatitis treating amount of a salt of Formula I or a hydrate thereof and a pharmaceutically acceptable carrier.

This invention is also directed to pharmaceutical compositions for the treatment of obesity in a mammal (including a human being) which comprise an obesity treating amount of a salt of Formula I or a hydrate thereof and a pharmaceutically acceptable carrier.

This invention is also directed to pharmaceutical compositions for the treatment of hypercholesterolemia in a mammal (including a human being) which comprise a hypercholesterolemia treating amount of a salt of Formula I or a hydrate thereof and a pharmaceutically acceptable carrier.

This invention is also directed to pharmaceutical compositions for the treatment of hypertriglyceridemia in a mammal (including a human being) which comprise a hypertriglyceridemia treating amount of a salt of Formula I or a hydrate thereof and a pharmaceutically acceptable carrier.

This invention is also directed to pharmaceutical compositions for the treatment of hyperlipidemia in a mammal (including a human being) which comprise a hyperlipidemia treating amount of a salt of Formula I or a hydrate thereof and a pharmaceutically acceptable carrier.

This invention is also directed to pharmaceutical compositions for the treatment of diabetes in a mammal (including a human being) which comprise a diabetes treating amount of a salt of Formula I or a hydrate thereof and a pharmaceutically acceptable carrier.

Another aspect of this invention is directed to methods for treating any of the disease states or conditions in which Apo B, serum cholesterol, and/or triglyceride levels are elevated.

Another aspect of this invention are methods for inhibiting or decreasing Apo B secretion in a mammal in need thereof which comprise the administration of an Apo B secretion inhibiting or decreasing amount of a salt of Formula I or a hydrate thereof.

Yet another aspect of this invention is directed to methods of treating atherosclerosis, pancreatitis, obesity, hypercholesterolemia, hypertriglyceridemia, hyperlipidemia or diabetes which comprise administering to a mammal, especially a human, in need of such treatment a therapeutically effective amount of a salt of Formula I or a hydrate thereof.

Yet another aspect of this invention is directed to methods of treating atherosclerosis which comprise administering to a mammal, especially a human, in need of such treatment a therapeutically effective amount of a salt of Formula I or a hydrate thereof.

Yet another aspect of this invention is directed to methods of treating pancreatitis which comprise administering to a mammal, especially a human, in need of such treatment a therapeutically effective amount of a salt of Formula I or a hydrate thereof.

Yet another aspect of this invention is directed to methods of treating obesity which comprise administering to a mammal, especially a human, in need of such treatment a therapeutically effective amount of a salt of Formula I or a hydrate thereof.

Yet another aspect of this invention is directed to methods of treating hypercholesterolemia which comprise administering to a mammal, especially a human, in need of such treatment a therapeutically effective amount of a salt of Formula I or a hydrate thereof.

Yet another aspect of this invention is directed to methods of treating hypertriglyceridemia which comprise administering to a mammal, especially a human, in need of such treatment a therapeutically effective amount of a salt of Formula I or a hydrate thereof.

Yet another aspect of this invention is directed to methods of treating hyperlipidemia which comprise administering to a mammal, especially a human, in need of such treatment a therapeutically effective amount of a salt of Formula I or a hydrate thereof.

Yet another aspect of this invention is directed to methods of treating diabetes which comprise administering to a mammal, especially a human, in need of such treatment a therapeutically effective amount of a salt of Formula I or a hydrate thereof.

The present invention is also directed to processes for preparing 4'-trifluoromethylbiphenyl-2-carboxylic acid-[2-(2-acetylaminoethyl)-1,2,3,4-tetrahydroisoquinolin-6-yl]-amide hydrochloride comprising combining the free base with hydrogen chloride in the presence of a suitable organic solvent.

The present invention is more particularly directed to a process as described in the immediately preceding paragraph wherein the solvent is ethyl acetate and methanol.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

As used herein, the expressions "reaction-inert solvent" and "inert solvent" refers to a solvent which does not interact with starting materials, reagents, intermediates or products in a manner which adversely affects the yield of the desired product.

Other features and advantages will be apparent from the specification and claims which describe the invention.

DETAILED DESCRIPTION OF THE INVENTION

Figure 1:
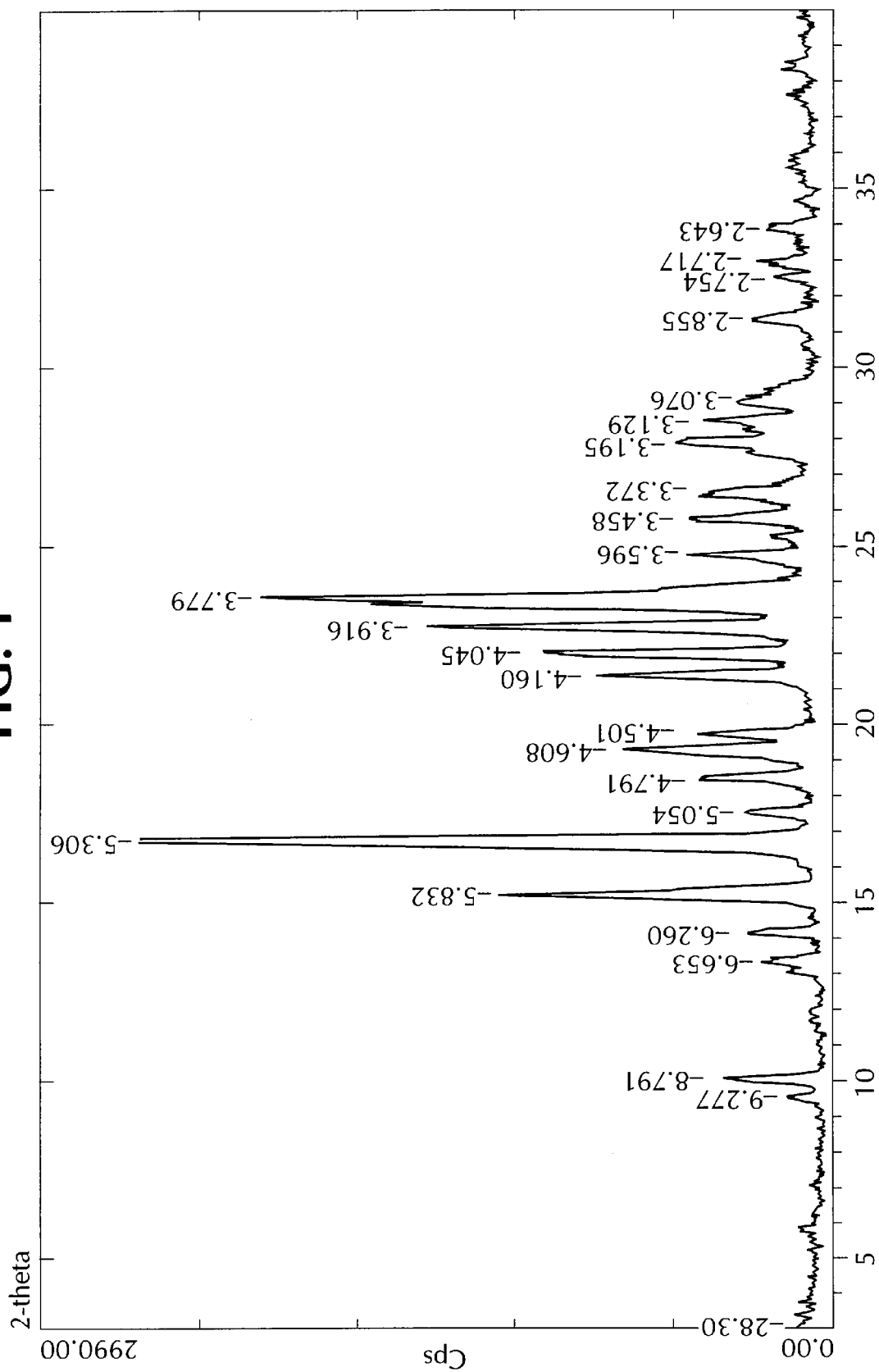
FIG. 1 is a characteristic x-ray powder diffraction pattern showing that 4'-trifluoromethylbiphenyl-2-carboxylic acid-[2-(2-acetylaminoethyl)-1,2,3,4-tetrahydroisoquinolin-6-yl]-amide hydrochloride is crystalline. (Vertical Axis: Intensity (CPS); Horizontal Axis: Two theta (degrees)).

The salt of the instant invention inhibits or decreases Apo B secretion, likely by the inhibition of MTP, although it may be possible that additional mechanisms are involved.

In general the salt of this invention can be made by processes which include analogous processes known in the chemical arts, particularly in light of the description contained herein. Certain processes for the manufacture of the salt of this invention are provided as further features of the invention and are illustrated by the following reaction schemes. Other processes may be described in the EXAMPLE section.

The free base of 4'-trifluoromethylbiphenyl-2-carboxylic acid-[2-(2-acetylaminoethyl)-1,2,3,4-tetrahydroisoquinolin-6-yl]-amide hydrochloride is prepared as disclosed below. The free base of the compound is isolated as a crystalline solid.

Referring to Scheme 1, 2-chloro-4-nitrobenzoic acid is treated with dimethyl malonate in the presence of base and a catalyst such as copper (I) bromide at a temperature of about 50° C. to about 100° C., preferably about 70° C. to form the formula 2 compound.

The formula 2 compound may then be treated with aqueous alcoholic base, conveniently at ambient temperature, to effect hydrolysis. The resulting compound is decarboxylated at a temperature of about 35° C. to about 100° C. to yield the formula 3 compound.

The formula 3 compound is reduced by exposure to a reducing agent such as borane (borane is made in situ from sodium borohydride and $BF_3$ etherate) in an aprotic solvent such as THF, at a temperature of about −25° C. to about 35° C.

The resulting formula 4 nitro diol is hydrogenated for example in the presence of a suitable catalyst such as platinum oxide in an aprotic solvent such as THF, conveniently at ambient temperature and elevated pressure (e.g., 50 p.s.i.) to form the corresponding aminodiol. The aminodiol is reacted with 4'trifluoromethylbiphenyl-2-carbonyl chloride in the presence of an amine base such as triethylamine in an aprotic solvent such as THF, conveniently at ambient temperature to afford the resulting formula 5 amide.

The formula 5 resulting amide is reacted with methanesulfonyl chloride in the presence of an amine base such as triethylamine and N-methylpyrrolidinone at a temperature of about −25° C. to about 25° C. The resulting compound is reacted with N-acetylethylenediamine in the presence of an amine base such as triethylamine and the temperature is allowed to rise to from about 25° C. to about 80° C. affording the freebase of the formula 6 compound of this invention.

The instant invention provides for an acid addition salt of compound I. The isoquinoline ring nucleus of compound I contains an isolated basic center and may therefore form an acid addition salt with various organic and inorganic conjugate acids. The hydrochloride salt is preferred and may be prepared as either the anhydrous or hydrate as follows.

A slurry of free base in a suitable solvent such as ethyl acetate is combined with an alcohol (e.g., methanol) solution of hydrogen chloride at room temperature yielding the anhydrous hydrochloride salt.

The hydrous hydrochloride salt may be prepared from the anhydrous hydrochloride salt by preparing an aqueous solution of the anhydrous hydrochloride salt conveniently at room temperature.

In addition, a polymorph of the anhydrous hydrochloride salt may be prepared by suspending the anhydrous hydrochloride salt in methylene chloride at reflux.

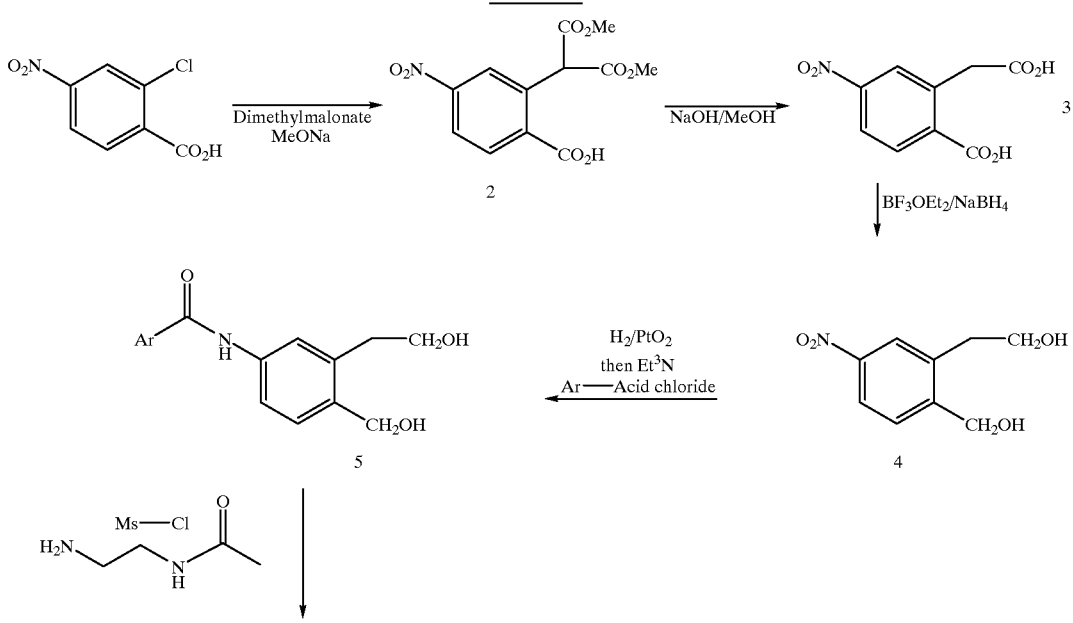

SCHEME 1

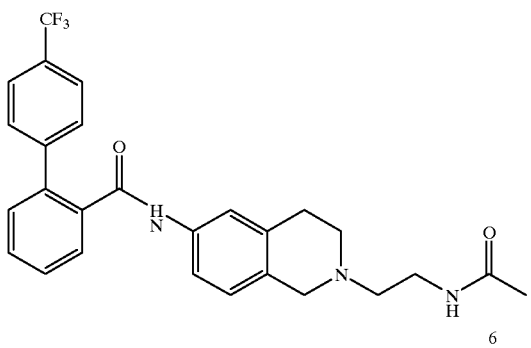

6

The hygroscopicity of the Formula I salt is measured using a moisture microbalance such as the VTI moisture balance (VTI Moisture Microbalances, MB 300 G and MB 300 W, VTI Corporation, Hialeah, Fla., USA). The Formula I salt is exposed to atmospheres having a range of humidity from 0% to 90% humidity. A temperature of 25° C. is maintained during all hygroscopicity measurements. The moisture adsorption and desorption isotherms of the anhydrous and hydrated HCl in atmospheres having humidity of 0% to 90% was determined using the VTI Moisture Microbalance. Anhydrous HCl and the monohydrate HCl were not hygroscopic over the range of humidities studied. Both the anhydrous HCl and the monohydrate HCl had superior hygroscopicity properties when compared to the mesylate salt (i.e., they absorbed less water). By comparison, the mesylate salt was extremely hygroscopic, deliquescing after isolation.

The compound of the instant invention is orally administrable and is accordingly used in combination with a pharmaceutically acceptable carrier or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described below. Thus, for oral administration the compound may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of the instant invention may also be administered parenterally. For parenteral administration the compounds may be combined with sterile aqueous or organic media to form injectable solutions or suspensions. Solutions or suspensions of these active compounds can be prepared in water suitably mixed with a surfactant such as hydroxypropylcellulose. If neccesary, the aqueous solutions should be suitably buffered and the liquid diluent first rendered isotonic with sufficient saline or glucose. In this capacity, the sterile aqueous media employed are all readily available by standard techniques well known to those of ordinary skill in the art. The parenterally administrable preparations may also be manufactured in the form of sterile solid compositions which can also be dissolved in sterile water, or some other sterile injectable medium immediately prior to intended use. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations may contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. They may be sterilized, for example, by filtration through a bacteria-retaining filter, by incorporating sterilizing agents into the compositions, or by irradiating or heating the compositions where such irradiating or heating is both appropriate and compatible with the drug formulation.

Additional pharmaceutical formulations may include, inter alia, suppositories, sublingual tablets, topical dosage forms and the like and these may be prepared according to methods which are commonly accepted in the art.

The dosage of the compound of the instant invention which is administered will generally be varied according to principles well known in the art taking into account the severity of the condition being treated and the route of administration. In general, the compound will be administered to a warm blooded animal (such as a human, livestock or pet) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1000 mg, preferably between 5 and 350 mg. The above dosages are exemplary of the average case; there can, of course, be individual instances where higher or lower doasge ranges are merited, and such deviations are within the scope of this invention.

EXAMPLES

Melting points were determined with a DSC apparatus. Unless otherwise stated, $CD_3OD$ was used for NMR spectra. Microanalysis was performed by Schwarzkopf Microanalytical Laboratory. All reagents and solvents were obtained commercially and used without purification.

Example 1

2-(Carboxy-5-nitro-phenyl)malonic acid dimethyl ester

A solution of 2-chloro-4-nitrobenzoic acid (75 g, 372 mmol) in dimethyl malonate (900 mL, 20 equivalents) was degassed with nitrogen for 15 min. Copper (I) bromide (5.4 g, 37 mmol) was added in one portion. Sodium methoxide (48.3 g, 894 mmol) was added in one portion to the solution while stirring and the contents exothermed to 48° C. Fifteen minutes later, the contents were heated to 70° C. for 24 hrs. The reaction was complete by nmr. Water (900 mL) was added to the cooled reaction followed by hexanes (900 mL). The aqueous layer was separated, toluene (900 mL) added, the solution filtered through Celite®, and the aqueous layer separated. Fresh toluene (1800 mL) was added to the aqueous layer and the biphasic mixture acidified with 6 N aqueous HCl (90 mL). A white precipitate formed and the contents were stirred for 18 hrs. The product was filtered off and dried to give a white solid, 78.1 g (70%, mp 153° C.). IR 2923, 2853, 1750, 1728, 1705, 1458, 1376, 1352, 1305, 1261 $cm^{-1}$. $^1H$ NMR $(CD_3)_2SO$ δ8.37(d,J=2 Hz, 1H), 8.30 (d,J=1 Hz,2H), 5.82(s, 1H),3.83 (s,6H).$^{13}C$ NMR $(CD_3)_2SO$ δ168.0, 167.3, 149.4, 137.1, 135.8, 132.5, 125.4, 123.7, 54.5, 53.4.Anal. Calcd for $C_{11}H_{10}NO_8$:C,48.49; H,3.73; N, 4.71. Found:C, 48.27; H,3.72; N, 4.76.

Example 2

2-Carboxymethyl-4-nitro-benzoic acid

Sodium hydroxide (10.10 g, 253 mmol) in water (120 mL) was added over 85 min to a solution of 2-(carboxy-5-nitro-phenyl)malonic acid dimethyl ester, (15.0 g, 51 mmol) in methanol (120 mL) at ambient temperature. After 3 hrs the reaction was complete, the methanol removed under vacuum, and the contents acidified with concentrated HCl (22.4 mL) at ambient temperature. The resulting white aqueous suspension was extracted twice with ethyl acetate (150 mL and 75 mL), the combined organic phases were dried with magnesium sulfate, and the volume of extracts reduced to 55 mL. The resulting ethyl acetate solution was heated to 65° C. for 6 hr effecting complete decarboxylation. The diacid was filtered off at ambient temperature and dried to afford 10 g of the diacid as a white solid (88%, mp 180–82° C.). IR 3080, 3055, 2983, 1707, 1611, 1585, 1516, 1491, 1424, 1358, 1298, 1237 $cm^{-1}$.$^1H$ NMR$(CD_3)_2O$δ12.87 (bs,2H),8.25(d,J=2 Hz, 1H),8.18 (dd,J=2 Hz, J=8 Hz,1H), 8.07(d,J=8 Hz,1H),4.07 (s,2H).$^{13}C$ NMR $(CD_3)_2SO$δ172.3, 167.5, 149.2, 138.8, 137.3, 132.1, 127,2, 122.4, 39.8. Anal. Calcd for $C_9H_{17}NO_6$:C,48.01; H,3.13; N,6.22.Found:C, 47.67; H, 3.19; N, 6.31.

Example 3

2-(2-Hydroxymethyl-5-nitro-phenyl)-ethanol

To a Tetrahydrofuran (THF) (220 mL) solution of 2-carboxymethyl-4-nitro-benzoic acid (10.0 g, 44.4 mmol) was added sodium borohydride (5.06 g, 133 mmol) in portions. The contents were cooled to 0° C., and boron trifluoride diethyl etherate (21.3 mL, 133 mmol) was added dropwise over 1 hr. The contents were allowed to warm to 25° C. and stirred for 16 hrs. The reaction was cooled to 0° C. and cautiously quenched with aqueous sodium hydroxide (1 N, 178 mL). The contents were stirred for 3 hrs, THF was removed under vacuum, the resulting aqueous suspension was cooled to 0° C. and the product was filtered off. After drying, the product was obtained as a white solid 7.78 g (89%, mp 79–81° C.). IR 3277, 3192, 2964, 2932, 1614, 1525, 1507, 1170, 1134, 1089, 1067 $cm^{-1}$.$^1H$ NMR $(CD_3)_2SO$ δ8.05 (d,J=9 Hz, 1H), 8.04 (s, 1H), 7.66 (d, J=9 Hz, 1H), 5.42 (t,J=5 Hz, 1H), 4.74 (t, J=5 Hz, 1H), 4.64 (d, J=5 Hz, 2H), 3.63 (m, 2H), 2.80 (t, J=6 Hz, 2H). $^{13}C$ NMR $(CD_3)_2SO$ δ149.1, 146.6, 139.2, 127.8, 124.3, 121.3, 61.2, 60.6, 34.9. Anal. Calcd for $C_9H_{11}NO_4$:C, 54.82; H, 5.62; N, 7.10. Found: C, 54.54; H, 5.49; N, 7.07.

Example 4

4'Trifluoromethylbiphenyl-2-carboxylic acid-[3-(2-hydroxyethyl)-4-hydroxymethylphenyl)]-amide A THF (100 mL) solution of 2-(2-hydroxymethyl-5-nitro-phenyl)-ethanol(10 g, 50.7 mmol) containing platinum oxide (0.5 g) was hydrogenated for 2 hr at 50 psi. The platinum oxide was filtered off through Celite® and THF (300 mL) was added to the filtrate. Triethylamine (14.2 mL, 193 mmol) was added followed by a THF (20 mL) solution of 4'trifluoromethylbiphenyl-2-carbonyl chloride(17.1 g, 60 mmol) and the contents were stirred for 18 hrs. The solvents were removed under vacuum, water (100 mL) was added and the contents were stirred for 1 hr. The crude product was filtered off and dried to afford 22.45 g. The crude product was suspended in methylene chloride (100 mL) and stirred for 1 hr. The purified product was filtered off and dried to afford a white solid (18.87 g, 90%). $^1H$ NMR $(CD_3)_2SO$ δ10.22 (S, 1H), 7.73 (d, J=8 Hz, 2H), 7.62–28 (m, 8H), 7.20 (d, J=8 Hz, 1H), 4.96 (bs, 1H), 4.69 (bs, 1H), 4.43 (s, 2H), 3.51 (t, J=7 Hz, 2H). 2.67 (t, J=7 Hz, 2H). IR(KBr) 3264, 3232, 31278, 3124, 3106, 2956, 2928, 1649, 1613, 1533, 1328, 1129 $cm^{-1}$. $^{13}C$ NMR $(CD_3)_2SO$ δ(amide CO) 167.7, aliphatic carbons 62.3, 61.1, 36.0. Anal. Calcd for $C_{23}F_3H_{20}NO_3$:C, 66,50; H, 4.85; N,3.37. Found: C, 66.29; H, 4.79; N, 3.27. MP 201–202° C.

Example 5

4'-Trifluoromethylbiphenyl-2-carboxylic acid-[2-(2-acetylaminoethyl)-1,2,3,4-tetrahydroisoquinolin-6-yl]-amide To 4'-trifluoromethylbiphenyl-2-carboxylic acid-[3-(2-hydroxyethyl)-4-hydroxymethylphenyl)]-amide (5.0 g, 12 mmol) and triethylamine (4.2 mL, 30 mmol) in N-methylpyrrolidinone (25 mL) at 0° C. was added methanesulfonyl chloride (2.0 mL, 26.4 mmol) dropwise over 5 min. The contents were stirred for 15 min, and additional triethylamine (2.1 mL) and methanesulfonyl chloride (1.0 mL) were added. After 15 min, N-acetylethylenediamine (6.13 g, 60 mmol) and triethylamine (8.2 mL) were added. The reaction contents were allowed to warm to 25 ° C. and stirred for 1 hr, then heated to 60° C. for 16 hr. The contents were cooled to 25° C., and basic water (13 mL of 1 N aqueous sodium hydroxide and 103 mL water) was added with stirring continuing for 4 hr. The crude product was filtered off, washed with water, and dried to afford 5.26 g (91% recovery) of an off white solid. The crude product was dissolved in refluxing ethanol (32 mL), hexanes were added (95 mL), seeded with authentic product, and the contents allowed to cool to 25° C. After stirring for 4 hr, the pure product was filtered off and dried to yield 2.62 g (45%) of the pure free base. $^{13}C(CD_3)_2SO\delta168.5$, 166.6, 143.8 137.4, 136.6, 136.3, 133.8, 129.7, 129.5, 129.4, 128.6, 127.5, 125.9, 124.6, 118.3, 116.8, 56.3, 54.5, 49.9, 28.2, 22.0. MP 163° C.

Example 6

4'-Trifluoromethylbiphenyl-2-carboxylic acid-[2-(2-acetylaminoethyl)-1,2,3,4-tetrahydroisoquinolin-6-yl]-amide hydrochloride; Anhydrous The synthesis begins by slow addition of 1.1 equivalents (1.9 mL) of 6.67 molar hydrogen chloride gas in methanol (9 g HCl in 37 mL MeOH) to a slurry of the free base, 4'-trifluoromethylbiphenyl-2-carboxylic acid-[2-(2-acetylaminoethyl)-1,2,3,4-tetrahydroisoquinolin-6-yl]-amide, (5.2 g) in ethyl acetate (73 mL) at room temperature. The free base dissolved on addition of the MeOH/HCl solution and the salt precipitated as flaky crystals from a hazy mixture within 45 minutes. The reaction mixture was stirred at 25° C. for 24 hours. The white solid was collected by filtration and dried under house vacuum at 45° C. (93% yield). The crystals melted at 220° C. with no degradation.

Anal. Calc.: C, 62.61; H, 5.25; N, 8.11; Cl, 6.84

Found: C, 62.38, H 5.23; N, 8.02; Cl, 6.77

According to FIG. 1 X-ray powder diffraction and polarized light microscopy (PLM) showed the anhydrous hydrochloride, 4'-trifluoromethylbiphenyl-2-carboxylic acid-[2-(2-acetylaminoethyl)-1,2,3,4-tetrahydroisoquinolin-6-yl]-amide hydrochloride was crystalline. The crystal habits encountered for the anhydrous hydrochloride 4'-trifluoromethylbiphenyl-2-carboxylic acid-[2-(2-acetylaminoethyl)-1,2,3,4-tetrahydroisoquinolin-6-yl]-amide hydrochloride were generally flakes; thin flat particles having similar length and width. The most intense reflections, d spacings, observed by x-ray powder diffraction were 5.832, 5.306, 4.160, 3.916, and 3.779 Å. (Vertical Axis: Intensity (CPS); Horizontal Axis: Two theta (degrees))

Example 7

4'-Trifluoromethylbiphenyl-2-carboxylic acid-[2-(2-acetylaminoethyl)-1,2,3,4-tetrahydroisoquinolin-6-yl]-amide hydrochloride; monohydrate The hydrate of the hydrochloride, 4'-trifluoromethylbiphenyl-2-carboxylic acid-[2-(2-acetylaminoethyl)-1,2,3,4-tetrahydroisoquinolin-6-yl]-amide hydrochloride-monohydrate was prepared utilizing the anhydrous hydrochloride. A solution of the anhydrous hydrochloride (10 g) in USP water (100 mL) was stirred at room temperature for 24 hours. The resulting thick creamy mixture was filtered and the crystals dried under vacuum at 45° C. for 48 hours (96% yield). Anal. Calc. C,60.50; H,5.45; N,7.84; Cl,6.61. Found: C,60.71; H5.50; N7.98; Cl,6.90. The crystals melted at 127° C.

Figure 2:
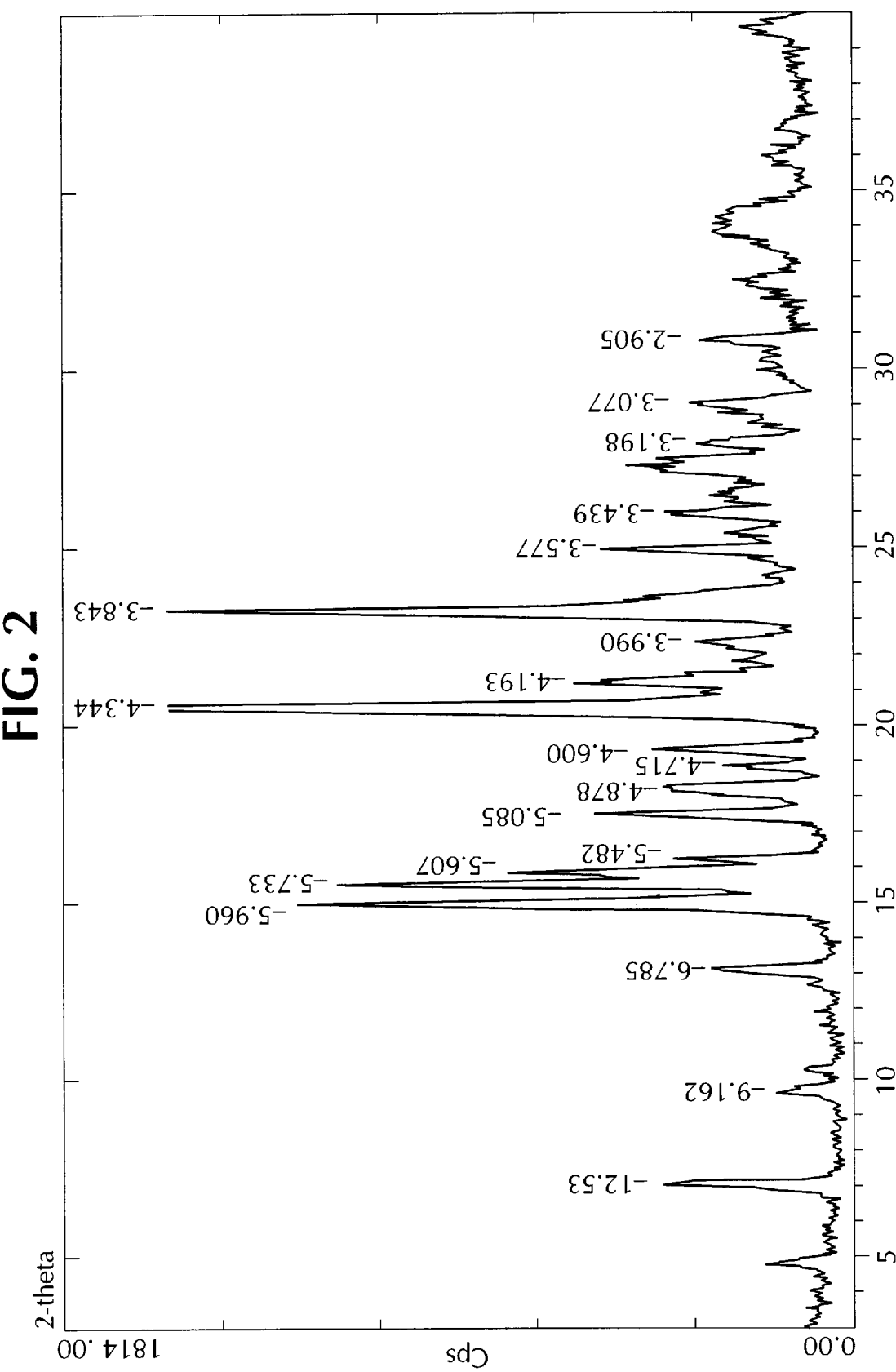
FIG. 2 is the characteristic x-ray powder diffraction pattern of the monohydrate crystalline 4'-trifluoromethylbiphenyl-2-carboxylic acid-[2-(2-acetylaminoethyl)-1,2,3,4-tetrahydroisoquinolin-6-yl]-amide hydrochloride (see Example 7 hereinafter). Vertical Axis: Intensity (CPS); Horizontal Axis: Two theta (degrees)).

According to FIG. 2 X-ray powder diffraction showed the monohydrate hydrochloride, 4'-Trifluoromethylbiphenyl-2-carboxyllic acid-[2-(2-acetylaminoethyl)-1,2,3,4-tetrahydroisoquinolin-6-yl]-amide hydrochloride was crystalline. The most intense reflections, d spacings, observed by x-ray powder diffraction were 5.960, 5.733, 4.344 and 3.843. (Vertical Axis: Intensity (CPS); Horizontal Axis: Two theta (degrees))

Example 8

4'-Trifluoromethylbiphenyl-2-carboxylic acid-[2-(2-acetylaminoethyl)-1,2,3,4-tetrahydroisoquinolin-6-yl]-amide hydrochloride;anhydrous polymorph Anhydrous hydrochloride (0.5 g) was suspended in methylene chloride (10 mL) and stirred at reflux for 24 hrs. MP 131° C.

Figure 3:
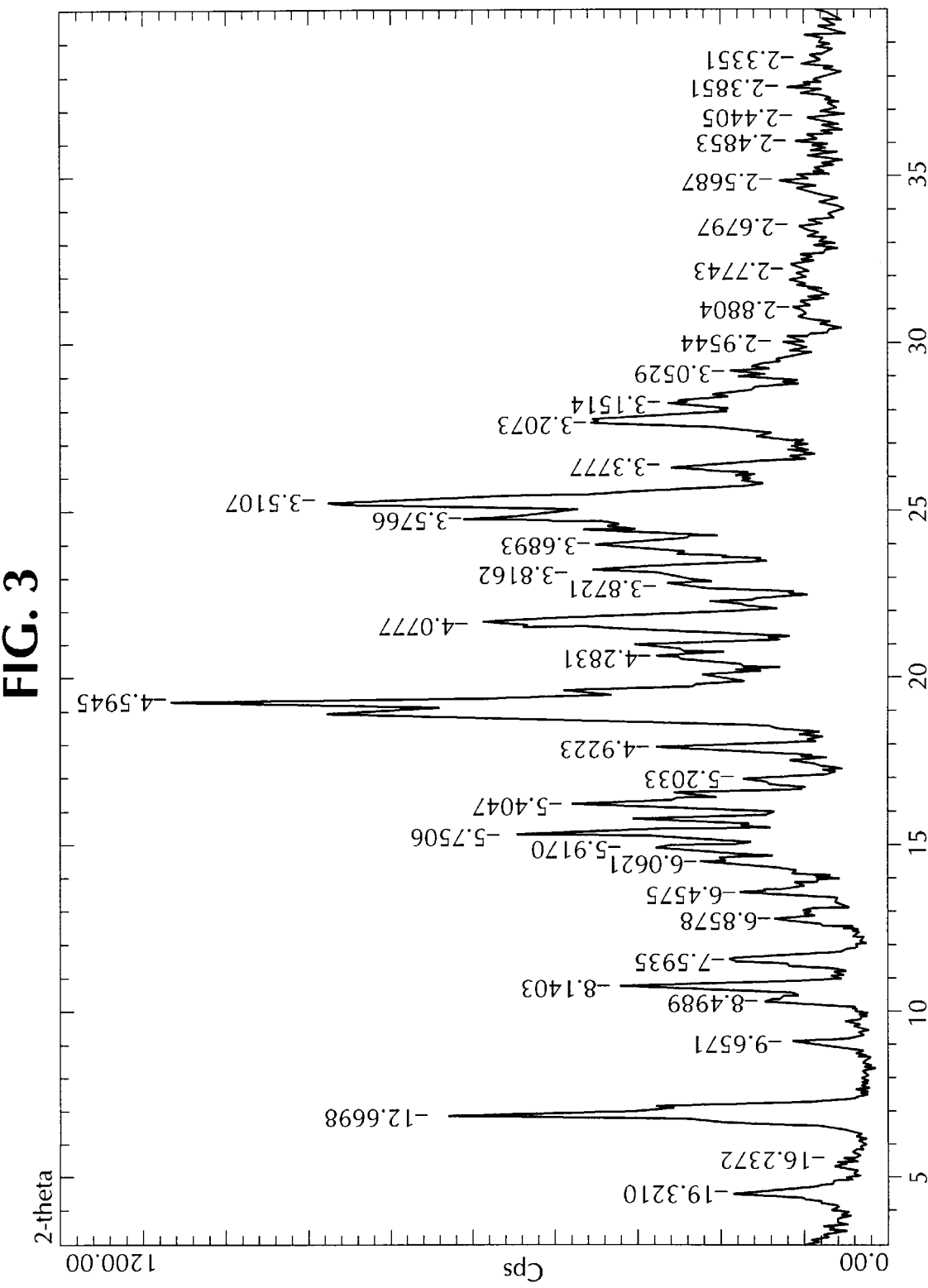
FIG. 3 is a characteristic x-ray powder diffraction pattern of anhydrous crystalline 4'-trifluoromethylbiphenyl-2-carboxylic acid-[2-(2-acetylaminoethyl) -1,2,3,4-tetrahydroisoquinolin-6-yl]-amide hydrochloride which is different from the form of the crystal depicted in FIG. 1 (see Example 8 hereinafter). Vertical Axis: Intensity (CPS); Horizontal Axis: Two theta (degrees)).

A sample of the resulting product was inspected using PLM and discrete crystalline needles of a high energy polymorph (0.31 g, 62% yield) were observed. According to FIG. 3, x-ray powder diffraction of an anhydrous polymorph of the hydrochloride, 4'-trifluoromethylbiphenyl-2-carboxylic acid-[2-(2-acetylaminoethyl)-1,2,3,4-tetrahydroisoquinolin-6-yl]-amide hydrochloride was observed as crystalline. This is a different form than the product of Example 6. The most intense reflections, d spacings, observed by x-ray powder diffraction were 12.669, 8.140, 5.750, 4.594, 4.077, 3.510 (Vertical Axis: Intensity (CPS); Horizontal Axis: Two theta (degrees)).

We claim:

1. The salt of Formula I

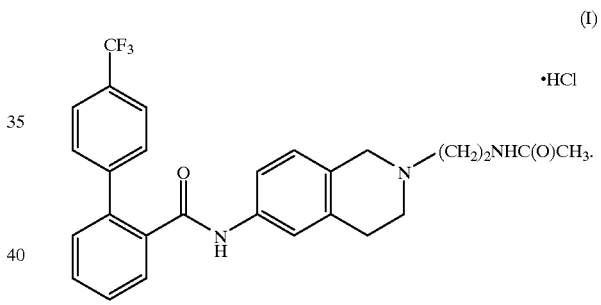

(I)

2. The salt of claim 1 which is anhydrous 4'-trifluoromethylbiphenyl-2-carboxylic acid-[2-(2-acetylaminoethyl)-1,2,3,4-tetrahydroisoquinolin-6-yl]-amide hydrochloride.

3. The salt of claim 1 which is the monohydrate of 4'-trifluoromethylbiphenyl-2-carboxylic acid-[2-(2-acetylaminoethyl)-1,2,3,4-tetrahydroisoquinolin-6-yl]-amide hydrochloride.

4. A pharmaceutical composition which comprises a therapeutically effective amount of the salt of claim 1 and a pharmaceutically acceptable carrier.

5. The pharmaceutical composition as recited in claim 4 wherein a hypertriglyceridemia treating amount of the Formula I salt is about 0.01 to 10 mg/kg/day.

6. The pharmaceutical composition as recited in claim 5 wherein the Formula I salt is anhydrous 4'-trifluoromethylbiphenyl-2-carboxylic acid-[2-(2-acetylaminoethyl)-1,2,3,4-tetrahydroisoquinolin-6-yl]-amide hydrochloride.

7. The pharmaceutical composition as recited in claim 5 wherein the Formula I salt is the monohydrate of 4'-trifluoromethylbiphenyl-2-carboxylic acid-[2-(2-acetylaminoethyl)-1,2,3,4-tetrahydroisoquinolin-6-yl]-amide hydrochloride.

8. A method of inhibiting or decreasing Apo B secretion in a mammal in need thereof which comprises the administration of an Apo B secretion inhibiting or decreasing amount of the Formula I salt as recited in claim 1.

9. The method as recited in claim 8 comprising treating atherosclerosis, pancreatitis, obesity, hypercholesterolemia, hypertriglyceridemia, hyperlipidemia or diabetes by administering to a mammal, in need of such treatment a therapeutically effective amount of the Formula I salt or a hydrate thereof.

10. The method as recited in claim 9 wherein hypertriglyceridemia is treated with a hypertriglyceridemia treating amount of the Formula I salt.

11. The method as recited in claim 10 wherein the hypertriglyceridemia treating amount of the Formula I salt is about 0.01 to 10 mg/kg/day.

12. The method as recited in claim 11 wherein the Formula I salt is anhydrous 4'-trifluoromethylbiphenyl-2-carboxylic acid-[2-(2-acetylaminoethyl)-1,2,3,4-tetrahydroisoquinolin-6-yl]-amide hydrochloride.

13. The method as recited in claim 11 wherein the Formula I salt is the monohydrate of 4'-trifluoromethylbiphenyl-2-carboxylic acid-[2-(2-acetylaminoethyl)-1,2,3,4-tetrahydroisoquinolin-6-yl]-amide hydrochloride.

14. A process for preparing 4'-trifluoromethylbiphenyl-2-carboxylic acid-[2-(2-acetylaminoethyl)-1,2,3,4-tetrahydroisoquinolin-6-yl]-amide hydrochloride comprising combining the free base of said compound with hydrogen chloride in the presence of a suitable organic solvent.

15. The process as recited in claim 14 wherein the hydrogen chloride is hydrogen chloride gas.

16. The process as recited in claim 15 wherein the solvent is ethyl acetate and methanol.

\* \* \* \* \*